(12) United States Patent
Sakakura et al.

(10) Patent No.: US 11,903,915 B2
(45) Date of Patent: Feb. 20, 2024

(54) POULTICE

(71) Applicant: HISAMITSU PHARMACEUTICAL CO., INC., Tosu (JP)

(72) Inventors: Tatsuya Sakakura, Tosu (JP); Satoshi Kimura, Tosu (JP); Seiichiro Tsuru, Tosu (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 113 days.

(21) Appl. No.: 17/429,683

(22) PCT Filed: Feb. 13, 2020

(86) PCT No.: PCT/JP2020/005599
§ 371 (c)(1),
(2) Date: Aug. 10, 2021

(87) PCT Pub. No.: WO2020/166665
PCT Pub. Date: Aug. 20, 2020

(65) Prior Publication Data
US 2022/0105060 A1    Apr. 7, 2022

(30) Foreign Application Priority Data

Feb. 14, 2019    (JP) ................... 2019-024287
Jan. 23, 2020    (JP) ................... 2020-009507

(51) Int. Cl.
*A61K 31/192*    (2006.01)
*A61K 9/70*    (2006.01)
*A61K 31/045*    (2006.01)
*A61K 47/10*    (2017.01)

(52) U.S. Cl.
CPC .......... *A61K 31/192* (2013.01); *A61K 9/7038* (2013.01); *A61K 31/045* (2013.01); *A61K 47/10* (2013.01)

(58) Field of Classification Search
None
See application file for complete search history.

(56) References Cited

U.S. PATENT DOCUMENTS

| | | |
|---|---|---|
| 5,232,702 A | 8/1993 | Pfister et al. |
| 6,239,177 B1 | 5/2001 | Mori et al. |
| 6,914,169 B1 | 7/2005 | Dota et al. |
| 10,123,977 B2 | 11/2018 | Tsurushima et al. |
| 10,940,121 B2 | 3/2021 | Tsuru et al. |
| 2004/0156886 A1 | 8/2004 | Kose |
| 2005/0181163 A1 | 8/2005 | Kose |
| 2007/0148216 A1 | 6/2007 | Yoshitake et al. |
| 2009/0043236 A1 | 2/2009 | Kawamura et al. |
| 2011/0097407 A1 | 4/2011 | Kamakura et al. |
| 2012/0102242 A1 | 4/2012 | Koren et al. |
| 2014/0302118 A1 | 10/2014 | Kawamura et al. |
| 2016/0175262 A1 | 6/2016 | Tsurushima et al. |
| 2016/0206569 A1 | 7/2016 | Tsurushima et al. |
| 2016/0361281 A1 | 12/2016 | Tsuru et al. |
| 2017/0348248 A1 | 12/2017 | Tsurushima et al. |

FOREIGN PATENT DOCUMENTS

| | | |
|---|---|---|
| CN | 1813702 A | 8/2006 |
| CN | 101184479 A | 5/2008 |
| CN | 102858332 A | 1/2013 |
| CN | 103313710 A | 9/2013 |
| CN | 105473132 A | 4/2016 |
| CN | 105960234 A | 9/2016 |
| CN | 107106511 A | 8/2017 |
| CN | 107106513 A | 8/2017 |
| EP | 0514794 A1 | 11/1992 |
| EP | 0965342 A1 | 12/1999 |
| EP | 1661583 A1 | 5/2006 |
| EP | 2545912 A1 | 1/2013 |
| JP | S60-4125 A | 1/1985 |
| JP | H03220120 A | 9/1991 |
| JP | 3-223212 A | 10/1991 |
| JP | H03223212 A | 10/1991 |
| JP | 4-346922 A | 12/1992 |
| JP | 5-65224 A | 3/1993 |
| JP | 0565224 A | 3/1993 |
| JP | 6-199701 A | 7/1994 |
| JP | H06199701 A | 7/1994 |
| JP | 9-315976 A | 12/1997 |
| JP | H09315976 A | 12/1997 |
| JP | 10-95728 A | 4/1998 |
| JP | 2837337 B2 | 12/1998 |
| JP | H11-12910 A | 1/1999 |
| JP | H11-188054 A | 7/1999 |
| JP | 2000143503 A | 5/2000 |

(Continued)

OTHER PUBLICATIONS

Non-Final Office Action dated Nov. 7, 2022 corresponding to U.S. Appl. No. 17/167,498.
Yan, Conqi, et al. "Rheological Properties of Peptide-Based Hydrogels for Biomedical and Other Applications"; NIH Public Access; Chem Soc Rev; Sep. 2010.
Extended European Search Report dated Oct. 19, 2022 corresponding to application No. 20755936.0-1109.
Taiwan Office Action dated Jun. 28, 2022 corresponding to application No. 109104562.
Н.А. Ляпунов, et al. "Identification and Assay of the Ketoprofen Esters"; Pharmaceutical Sciences, vol. 41, No. 3; State Scientific Institution «Institute for Single Crystals» of NAS of Ukraine; 2018.

(Continued)

*Primary Examiner* — Kyung S Chang
(74) *Attorney, Agent, or Firm* — Nath, Goldberg & Meyer; Joshua B. Goldberg

(57) ABSTRACT

The present invention provides a gel patch having a paste layer on a support, wherein the paste layer comprising ketoprofen or a pharmaceutically acceptable salt thereof, propylene glycol, 1-menthol, and water, wherein the mass of propylene glycol in the paste layer is 3-fold the mass of ketoprofen or less, and wherein the content of 1-menthol based on a total mass of the paste layer is 0.1 to 0.5 mass %.

2 Claims, No Drawings

(56) References Cited

FOREIGN PATENT DOCUMENTS

| | | | |
|---|---|---|---|
| JP | 2001-302503 A | 10/2001 |
| JP | 2002187836 A | 7/2002 |
| JP | 2003-155252 A | 5/2003 |
| JP | 2004067562 A | 3/2004 |
| JP | 2006-8593 A | 1/2006 |
| JP | 20068593 A | 1/2006 |
| JP | 2007-39451 A | 2/2007 |
| JP | 2007-269712 A | 10/2007 |
| JP | 2007-320939 A | 12/2007 |
| JP | 2007-326844 A | 12/2007 |
| JP | 2007326844 A | 12/2007 |
| JP | 2008037798 A | 2/2008 |
| JP | 4346922 B2 | 10/2009 |
| JP | WO2012102242 A1 | 8/2012 |
| JP | 2013-82650 A | 5/2013 |
| JP | 2019-81755 A | 5/2019 |
| KR | 1020010111593 A | 12/2001 |
| KR | 1020080015120 A | 2/2008 |
| TW | 337086 B1 | 2/2011 |
| TW | I337086 B1 | 2/2011 |
| TW | 630930 B1 | 8/2018 |
| TW | I630930 B | 8/2018 |
| WO | 9728793 A1 | 8/1997 |
| WO | 0183866 A2 | 11/2001 |
| WO | 02100384 A1 | 12/2002 |
| WO | 03082164 A1 | 10/2003 |
| WO | 2004047820 A1 | 6/2004 |
| WO | 2006/070672 A1 | 7/2006 |
| WO | 2006/090782 A1 | 8/2006 |
| WO | 2006090782 A1 | 8/2006 |
| WO | 2006/129745 A1 | 12/2006 |
| WO | 2010073327 A1 | 7/2010 |
| WO | 2012102242 A1 | 8/2012 |
| WO | 2013/027840 A1 | 2/2013 |
| WO | 2015025935 A1 | 2/2015 |
| WO | 2015129808 A1 | 9/2015 |

OTHER PUBLICATIONS

"Medical supply interview form MOHRUS PAP XR 120mg", https://www.info.pmda.go.jp/go/Interview/1/650034_2649729S6024_1_1F.pdf, , Apr. 2018 revised edition, p. 1-p. 40.

"Instructions for medical supply interview form 2018", Japanese Society of Hospital Pharmacists [online] https://www.jshp.or.jp/cont/18/1108-2-3.pdf, 2018, p. 1-p. 14.

Yan, Congi, et al. "Rheological Properties of Peptide-based Hydrogels for Biomedical and Other Applications"; NIH Public Access; Chem Soc Rev; Sep. 2010.

International Search Report dated Mar. 15, 2016 issued in corresponding International Application No. PCT/JP2016/054570.

Office Action dated Oct. 13, 2020 corresponding to BR Patent Application No. BR1120170172879.

Chinese Office Action dated May 29, 2020 corresponding to application No. 201680004916.1.

Office Action dated Apr. 8, 2019 issued in Taiwanese Patent Application No. 105105313.

International Preliminary Report on Patent ability dated Sep. 8, 2017 in corresponding counterpart International Patent Application No. PCT/JP2016/054570.

Meng, Shengnan, "Pharmacology", Sep. 2011, p158.

Zhang, Yuan, "Chinese medicine formulation technology", Aug. 2012, p. 262-p. 263, p. 280.

Extended European search report dated Jul. 18, 2018 for corresponding application No. 16755303.1.

JSL (Japaneses Industrial Standard) L 1018, 1999, pp. 819, 822, and 826.

Japanese Office Action dated Apr. 14, 2020 corresponding to application No. 2016-566128.

Wang et al., Rheological Characterization of Cataplasm Bases Composed of Cross-linked Partially Neutralized Polyacrylate Hydrogel, AAPS PharmSciTech, 15(5), pp. 1149-1154. (Year: 2014).

Cilurzo et al., Expert Opin. Drug Deliv., 9(1), pp. 33-45. (Year: 2012).

International Search Report dated Mar. 31, 2020 corresponding to application No. PCT/JP2020/005599.

Taiwan Office Action dated Jan. 28, 2022 corresponding to application No. 109104562.

Lyapunov, et al. "Identification and Assay of the Ketoprofen Esters"; State Scientific Institution «Institute for Single Crystals» of NAS of Ukraine; vol. 31, No. 3; 2018.

International Preliminary Report on Patentability (IPRP) dated Aug. 26, 2021 corresponding to application No. PCT/JP2020/005599.

Japanese Office Action dated Mar. 22, 2022 corresponding to application No. P2020-009507.

The Extended European Search Report dated Oct. 19, 2022 corresponding to application No. 20755936.0-1109.

Notice of Allowance dated Apr. 18, 2023 corresponding to Japanese application No. P2020-009507.

POULTICE

TECHNICAL FIELD

The present invention relates to a gel patch and a method of producing the same.

BACKGROUND ART

A gel patch is one type of adhesive produced by spreading a paste layer containing a drug on a support such as a cloth, and generally contains a large amount of water, and the paste layer is thick and causes little irritation to the skin. In addition, the adhesion strength of the gel patch often decreases with the elapse of time after application, and the development of a gel patch of which the adhesion strength is unlikely to decrease even after application for a long time has been studied (Patent Literatures 1 to 4).

Patent Literature 1 discloses that a decrease in the adhesion strength can be reduced by adding poly(methyl acrylate/2-ethylhexyl acrylate) to a gel patch containing a partially neutralized polyacrylic acid. In particular, Patent Literature 2 discloses that, when a polyacrylic acid is additionally added to a paste layer, a gel patch having excellent moldability and shape retention can be obtained. In addition, since the drug is contained in a water-containing paste layer, the gel patch tends to reduce the skin permeability of the drug compared with a tape agent (for example, Patent Literature 3).

CITATION LIST

Patent Literature

[Patent Literature 1] WO 2006/090782 A
[Patent Literature 2] WO 2015/025935 A
[Patent Literature 3] WO 2015/129808 A
[Patent Literature 4] JP H10-95728 A

SUMMARY OF INVENTION

Technical Problem

The inventors studied the development of a gel patch containing ketoprofen as an active component and found that a part of ketoprofen is easily converted into an ester analogue due to a transesterification or the like during storage of the gel patch. Here, an object of the present invention is to provide a gel patch having excellent storage stability with respect to ketoprofen.

In addition, the inventors have found that, after a gel patch containing poly(methyl acrylate/2-ethylhexyl acrylate) is applied for one day, the peel strength of the paste layer becomes higher, and pain may occur during peeling off. Here, another object of the present invention is to provide a gel patch of which the adhesion strength is not reduced even after application for one day and the peel strength is unlikely to increase.

Solution to Problem

[1] A gel patch having a paste layer on a support, wherein the paste layer comprises ketoprofen or a pharmaceutically acceptable salt thereof, propylene glycol, 1-menthol, and water, wherein the mass of propylene glycol in the paste layer is 3-fold the mass of ketoprofen or less, and wherein the content of 1-menthol based on a total mass of the paste layer is 0.1 to 0.5 mass %.

[2] The gel patch in which the paste layer further comprises at least one of poly(methyl acrylate/2-ethylhexyl acrylate) and poly(methacrylic acid/n-butyl acrylate).

[3] The gel patch according to [1] or [2], wherein the paste layer further comprises at least one of a fatty acid alkyl ester and an alkylene dicarboxylic acid ester.

[4] The gel patch according to [3], wherein the loss modulus of the paste layer after being left under an environment of a temperature of 25° C. and a relative humidity of 55% for 24 hours after a release liner is peeled off is 3,000 to 7,000 Pa under conditions of a frequency of 15 Hz and a measurement temperature of 32° C.

[5] The gel patch according to [3] or [4], wherein the fatty acid alkyl esters comprise at least one selected from the group consisting of hexyl laurate, isopropyl myristate and isopropyl palmitate.

[6] The gel patch according to any one of [3] to [5], wherein the alkylene dicarboxylic acid esters comprise diisopropyl adipate.

[7] A method of stabilizing ketoprofen in a gel patch having a paste layer comprising ketoprofen or a pharmaceutically acceptable salt thereof on a support, including adding a mass of propylene glycol 3-fold the mass of ketoprofen or less to the paste layer.

[8] A gel patch having a paste layer on a support and additionally having a release liner on the side opposite to the support with respect to the paste layer,
wherein the paste layer comprises a physiologically active substance, water, at least one of poly(methyl acrylate/2-ethylhexyl acrylate) and poly(methacrylic acid/n-butyl acrylate), and at least one of a fatty acid alkyl ester and an alkylene dicarboxylic acid ester, and
wherein the loss modulus of the paste layer after being left under an environment of a temperature of 25° C. and a relative humidity of 55% for 24 hours after the release liner is peeled off is 3,000 to 7,000 Pa under conditions of a frequency of 15 Hz and a measurement temperature of 32° C.

[9] The gel patch according to [8], wherein the physiologically active substance is ketoprofen or a pharmaceutically acceptable salt thereof.

[10] The gel patch according to [8] or [9], further comprising a fatty acid alkyl ester or an alkylene dicarboxylic acid ester.

[11] The gel patch according to any one of [8] to [10], wherein the fatty acid alkyl esters comprise at least one selected from the group consisting of hexyl laurate, isopropyl myristate and isopropyl palmitate.

[12] The gel patch according to any one of [8] to [11], wherein the alkylene dicarboxylic acid esters comprise diisopropyl adipate.

[13] The gel patch according to any one of [8] to [12], further comprising propylene glycol.

[14] The gel patch according to [13], wherein the mass of propylene glycol is 3-fold the mass of the physiologically active substance or less.

Advantageous Effects of Invention

According to the present invention, it is possible to provide a gel patch having excellent storage stability with respect to ketoprofen. When the storage stability with respect to ketoprofen is improved, the expiration date of the gel patch as a pharmaceutical product can be further extended, and the gel patch can also be beneficial in consideration of stable supply of pharmaceutical products, reduction in economic burden on users, reduction in environmental burden, and the like.

In this specification, "excellent storage stability with respect to ketoprofen" means that the amount of ketoprofen ester produced is small, and for example, after storage at 60° C. for 2 weeks, when the content of ketoprofen ester analogues in the paste layer based on the content of ketoprofen immediately after the gel patch is prepared is 2.1% or less and preferably 1.9% or less, it can be determined that storage stability with respect to ketoprofen is excellent. When the content of the ketoprofen ester analogues is 2.1% or less, even two years after production, a sufficient therapeutic effect of ketoprofen as a pharmaceutical product can be exhibited.

According to the present invention, it is possible to provide a gel patch that not only has excellent adhesiveness but also has an adhesion strength that is not reduced even after application for one day and a peel strength that is unlikely to increase.

In this specification, "adhesiveness is excellent" means that, in a probe tack test, after a specified cylindrical probe is brought into contact with an adhesive surface of an adhesive for a short time, a measured value of the strength in peeling off (peel strength) is 0.2 N or more, or in a tilt type ball tack test, when a gel patch is arranged on an inclined plate provided at an tilt angle of 30° so that the support surface is in contact with the inclined plate, a release liner is peeled off, and a ball having a size with a diameter of 9/32 inches or more is disposed at a position of 100 mm from the upper end of the support, the ball stops on the paste layer. The distance from the upper end of the support to the position at which the ball is disposed is called a runway. The probe tack test can be performed according to the description of the Japanese Pharmacopoeia 17$^{th}$ edition. The tilt type ball tack test can be performed according to the description of JIS Z0237:2009 or the Japanese Pharmacopoeia 17$^{th}$ edition.

In this specification, "peel strength increases" means that the numerical value of the peel strength of the paste layer after storage under a predetermined environment is larger than the numerical value of the peel strength of the paste layer when production of the gel patch is completed.

In this specification, a high frequency range, which is a loss modulus measurement condition, is a range of 15 to 50 Hz. According to the Adhesive Handbook 3$^{rd}$ edition (Japan Adhesive Tape Manufacturers Association, published in 2005), the frequency related to the breakage procedure such as peeling and tack is $10^2$ rad/s (about 16 Hz), the frequency related to the contact procedure such as finger tack, polyken probe tack, or loop tack is 10 to $10^{-1}$ rad/s (about 0.016 to 1.6 Hz), and the frequency related in the shear deformation process in the holding force test is $10^{-2}$ rad/s (about 0.0016 Hz).

DESCRIPTION OF EMBODIMENTS

Hereinafter, preferred embodiments of the present invention will be described below in detail.

A first embodiment of the present invention is a gel patch having a paste layer on a support, in which the paste layer contains ketoprofen or a pharmaceutically acceptable salt thereof, propylene glycol, 1-menthol, and water, the mass of propylene glycol in the paste layer is 3-fold the mass of ketoprofen or less, and the content of 1-menthol based on a total mass of the paste layer is 0.1 to 0.5 mass %.

The support may be any one that can support a paste containing water, and those well-known to those skilled in the art can be used. Examples of supports include woven fabrics (including knitted fabrics), non-woven fabrics, resin films, foam sheets and paper. When a woven fabric, a non-woven fabric or a resin film is used as the support, examples of materials thereof include polyolefins such as polyethylene, polypropylene, and polybutylene, polyesters such as polyethylene terephthalate, rayon, polyurethane and cotton, and these may be used alone or two or more thereof may be used in combination. Polyester is more preferable as the material of the support.

The support is preferably a non-woven fabric or a woven fabric, and a non-woven fabric or woven fabric having a predetermined elongation recovery rate (elongation elastic modulus) is particularly preferable. In this specification, "elongation recovery rate" is a value measured according to the description of JIS L1096:2010, and means an "elongation elastic modulus at constant load" or an "elongation elastic modulus during constant rate elongation." For example, "50% elongation recovery rate" is an elongation elastic modulus when elongation (constant rate elongation) is performed so that the elongation percentage becomes 50%, and "load at 50% elongation" is a load (constant load) required for elongation so that the elongation percentage becomes 50%. When a non-woven fabric or woven fabric having a predetermined elongation recovery rate is used, this is preferable because the support expands according to a movement of an application part when it is applied to a moving part such as a joint.

When the support is a non-woven fabric, for example, the 50% elongation recovery rate of the non-woven fabric is 60 to 99%, preferably 65 to 95%, and more preferably 70 to 90%. In addition, the load at 50% elongation of the non-woven fabric is preferably, for example, 1 to 5 N/2.5 cm in the vertical direction (long axis direction) and 0.1 to 3 N/2.5 cm in the lateral direction (minor axis direction). The basis weight of a preferable support is, for example, 80 to 120 g/m$^2$, and preferably 90 to 110 g/m$^2$. The thickness of a preferable support is, for example, 0.5 to 2 mm. In addition, the stiffness of the support (the stiffness measurement method is the A method (45° cantilever method) according to JIS L1096: 2010) can be, for example, 20 to 40 mm in the vertical direction (long axis direction) and 10 to 35 mm in the lateral direction (short axis direction), and is preferably 25 to 35 mm in the vertical direction (long axis direction) and 15 to 30 mm in the lateral direction (short axis direction).

The thickness of the non-woven fabric as the support is preferably 0.5 to 2 mm. The basis weight of the non-woven fabric as the support is preferably 80 to 150 g/m$^2$.

The knitted fabric used as the support also includes, for example, a knitted fabric in which stitches are assembled into a cloth shape by circular knitting, warp (vertical) knitting, weft (horizontal) knitting, or the like. Knitted fabrics made of one or a combination of two or more of polyester, nylon, polypropylene, and rayon materials are preferable, and among these, a knitted fabric made of polyethylene terephthalate is more preferable because it has a weak interaction with drugs.

In particular, when the support is a woven fabric, the 50% elongation recovery rate of the woven fabric is, for example, 60 to 99%, preferably 65 to 95%, and more preferably 70 to 90%. In addition, the load at 50% elongation is preferably, for example, 1 to 5 N/2.5 cm in the vertical direction (long axis direction) and 0.1 to 3 N/2.5 cm in the lateral direction (minor axis direction). The stiffness of the support can be, for example, 10 to 30 mm in the vertical direction (long axis direction) and 10 to 30 mm in the lateral direction (minor axis direction), and is preferably 15 to 25 mm in the vertical direction (long axis direction) and 15 to 25 mm in the lateral direction (minor axis direction).

The thickness of the woven fabric as the support is preferably 0.5 to 2 mm.

In particular, when the polyethylene terephthalate woven fabric has a basis weight of 80 to 150 g/m$^2$, water contained in the paste is less likely to exude through the mesh of the woven fabric during spreading, and the anchoring property between the woven fabric and the paste becomes better.

In addition, it is preferable for the polyethylene terephthalate woven fabric to have a vertical direction (long axis direction) modulus of 2 to 12 N/5 cm and a lateral direction (minor axis direction) modulus of 2 to 8 N/5 cm (the method of measuring a modulus is based on JIS L1018: 1999). If the modulus is lower than 2 N/5 cm, when the paste spreads, the woven fabric may be stretched, the adhesive may soak into the mesh, and the function of the gel patch may deteriorate. In addition, if the modulus is larger than 12 N/5 cm (vertical direction) or 8 N/5 cm (lateral direction), the elasticity deteriorates and it may be difficult to follow the stretch of the skin when it is applied to the moving part.

The paste layer contains ketoprofen or a pharmaceutically acceptable salt thereof, propylene glycol, and water.

Ketoprofen is a compound represented by Chemical Formula (1), and there are two types of optical isomers: R-form and S-form. In the present embodiment, ketoprofen of any one optical isomer may be used, or a mixture containing two types of optical isomers at an arbitrary ratio may be used.

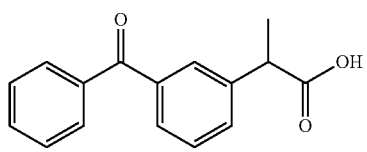

(1)

Examples of pharmaceutically acceptable salts of ketoprofen include inorganic salts such as sodium salts, potassium salts, and calcium salts; and amine salts such as monoethanolamine and diethanolamine.

The content of ketoprofen in the paste layer based on a mass of the entire paste layer is 1.5 to 2.5 mass % and preferably 1.8 to 2.2 mass %. Here, when the paste layer contains a pharmaceutically acceptable salt of ketoprofen, the mass of the salt is converted into the mass of ketoprofen.

Propylene glycol has a particularly excellent effect of improving the skin permeability of ketoprofen. The content of propylene glycol in the paste layer based on mass is 3 times or less, and may be 0.5 to 3-fold, 0.7 to 3-fold, 1 to 3-fold, 0.5 to 2.5-fold, 0.7 to 2.5-fold, 1 to 2.5-fold, or 1.5 to 2.5-fold the content of ketoprofen.

The content of propylene glycol in the paste layer based on a total mass of the paste layer may be 1.5 to 6.5 mass %, 2.5 to 6.5 mass %, or 3 to 6 mass %.

The content of water in the paste layer based on a total mass of the paste layer may be 30 to 60 mass % or 35 to 50 mass %.

The paste layer may further contain at least one of a fatty acid alkyl ester and an alkylene dicarboxylic acid ester. The fatty acid alkyl ester may be an ester synthesized from a fatty acid and an alkyl alcohol (alkanol). The alkyl alcohol may be, for example, an alkyl alcohol having 1 to 10 carbon atoms. In this specification, the fatty acid means a saturated or unsaturated alkylcarboxylic acid having 8 to 18 carbon atoms. Examples of fatty acid alkyl esters include caprylic acid alkyl ester, capric acid alkyl ester, lauric acid alkyl ester, myristic acid alkyl ester, palmitic acid alkyl ester, palmitoleic acid alkyl ester, stearic acid alkyl ester, and oleic acid alkyl ester. A preferable fatty acid alkyl ester is hexyl laurate or isopropyl myristate. Fatty acid alkyl esters may be used alone or two or more thereof may be used in combination. When a fatty acid alkyl ester is contained, the skin permeability of ketoprofen can be improved. When a fatty acid alkyl ester is contained, the loss modulus can be adjusted to within a predetermined range and the skin permeability of the physiologically active substance can be improved.

The content of the fatty acid alkyl ester in the paste layer based on a total mass of the paste layer may be 1 to 20 mass % and is preferably 1 to 15 mass % or 2 to 13 mass %. In particular, the content of hexyl laurate, isopropyl myristate or isopropyl palmitate based on a total mass of the paste layer may be 0.5 to 15 mass % or 0.5 to 10 mass % and is preferably 0.5 to 5.0 mass % or 1.0 to 3.5 mass %. When the content of hexyl laurate, isopropyl myristate or isopropyl palmitate is 0.5 to 5.0 mass %, the skin permeability of ketoprofen is particularly excellent, the loss modulus can be easily adjusted to within a predetermined range, and the skin permeability of the physiologically active substance is also excellent.

The alkylene dicarboxylic acid ester may be an ester synthesized from an alkylene dicarboxylic acid and a linear or branched alkyl alcohol. The alkyl alcohol may be, for example, an alkyl alcohol having 1 to 10 carbon atoms. In this specification, the alkylene dicarboxylic acid is a compound having a carboxyl group at both ends of an alkylene group having 1 to 8 carbon atoms. Examples of such alkylene dicarboxylic acids include ethandioic acid (oxalic acid), propanedioic acid (malonic acid), butanedioic acid (succinic acid), pentanedioic acid (glutaric acid), hexanedioic acid (adipic acid), heptanedioic acid (pimelic acid), octanedioic acid (suberic acid), nonanedioic acid (azelaic acid), and decanedioic acid (sebacic acid). Specific examples of alkylene dicarboxylic acid esters include diethyl adipic acid, diisopropyl adipate, diethyl sebacate, and diisopropyl sebacate. Alkylene dicarboxylic acid esters may be used alone or two or more thereof may be used in combination. In addition, the above fatty acid alkyl ester and alkylene dicarboxylic acid ester may be combined.

The content of the alkylene dicarboxylic acid ester in the paste layer based on a total mass of the paste layer may be 1 to 20 mass %, and is preferably 1 to 15 mass % or 2 to 13 mass %. In particular, the content of the diisopropyl adipate based on a total mass of the paste layer may be 0.5 to 10 mass % and is preferably 0.5 to 5.0 mass % or 1.0 to 3.5 mass %. When the content of the diisopropyl adipate is 0.5 to 5.0 mass %, the loss modulus can be easily adjusted to within a predetermined range, and the skin permeability of the physiologically active substance is particularly excellent.

A total content of the fatty acid alkyl ester and the alkylene dicarboxylic acid ester based on a total mass of the paste layer may be 1 to 10 mass %.

The paste layer may further contain a neutralized polyacrylic acid. The neutralized polyacrylic acid may be a completely neutralized polyacrylic acid, a partially neutralized polyacrylic acid, or a mixture thereof. Examples of neutralized polyacrylic acids include polyacrylates, and for example, sodium salts, potassium salts, calcium salts, and ammonium salts can be used.

The neutralized polyacrylic acid is preferably a partially neutralized polyacrylic acid because an initial adhesion strength and an adhesion strength over time are strong. The partially neutralized polyacrylic acid is one in which there are a structural unit derived from an acrylic acid and a structural unit derived from an acrylate at an arbitrary ratio in one polymer chain. Regarding the partially neutralized polyacrylic acid, one in which 50 mol % of carboxyl groups in one polymer chain are neutralized is preferably used.

The content of the neutralized polyacrylic acid in the paste layer based on a total mass of the paste layer is preferably 1 to 6 mass % and more preferably 2 to 6 mass %. When the content of the neutralized polyacrylic acid is 1 mass % or more, the adhesion strength of the paste layer is sufficiently high and it becomes unlikely to fall off. When the content of the neutralized polyacrylic acid is 6 mass % or less, the moldability and shape retention of the paste layer are improved.

The paste layer may further contain polyacrylic acid. When polyacrylic acid is contained, the maintenance performance of the adhesion strength is kept high and the shape retention of the gel patch is improved. The content of polyacrylic acid based on a mass of the paste layer is preferably 1 to 5 mass %. When the content of polyacrylic acid is 1 mass % or more, the moldability and shape retention of the paste layer are improved. When the content of polyacrylic acid is 5 mass % or less, the hardness of the paste layer is less likely to increase and the adhesion to the skin increases. When both the neutralized polyacrylic acid and polyacrylic acid are contained, the stickiness, moldability, shape retention and hardness of the gel patch are improved in a well-balanced manner.

The paste layer may further contain poly(methyl acrylate/2-ethylhexyl acrylate) or poly(methacrylic acid/n-butyl acrylate). Poly(methyl acrylate/2-ethylhexyl acrylate) is a copolymer of methyl acrylate and 2-ethylhexyl acrylate. Poly(methacrylic acid/n-butyl acrylate) is a copolymer of methacrylic acid and n-butyl acrylate. The content proportion of each monomer is not particularly limited.

Poly(methyl acrylate/2-ethylhexyl acrylate) or poly(methacrylic acid/n-butyl acrylate) may be in the form of an emulsion (aqueous emulsion) in which it is dispersed in any solvent such as water or an aqueous organic solvent. Examples of aqueous emulsions of poly(methyl acrylate/2-ethylhexyl acrylate) include Nikasol TS-620 (product name, commercially available from Nippon Carbide Industries Co., Inc.). Examples of aqueous emulsions of poly(methacrylic acid/n-butyl acrylate) include Primal N-580NF (product name, commercially available from Rohm and Haas Company), UltraSol W-50 (product name, commercially available from Aica Kogyo Co., Ltd.). When a paste solution for a gel patch is prepared, these copolymers are mixed with other components in the form of an aqueous emulsion, and these polymers are easily dispersed throughout the paste solution. When these copolymers are dispersed throughout the paste layer, a more significant effect of minimizing a decrease in the adhesion strength is obtained, and even after application for a longer time, sufficient adhesion strength can be exhibited.

The content of poly(methyl acrylate/2-ethylhexyl acrylate) or poly(methacrylic acid/n-butyl acrylate) based on a total mass of the paste layer may be 2.75 to 15.75 mass % and is preferably 3.3 to 13.86 mass %, 5.5 to 12.6 mass % or 5.5 to 11.34 mass % in terms of a solid content.

The content of the aqueous emulsion of poly(methyl acrylate/2-ethylhexyl acrylate) or poly(methacrylic acid/n-butyl acrylate) based on a total mass of the paste layer may be 5 to 25 mass % (2.75 to 15.75 mass % in terms of a solid content) and is preferably 6 to 22 mass % (3.3 to 13.86 mass % in terms of a solid content), 10 to 20 mass % (5.5 to 12.6 mass % in terms of a solid content) or 10 to 18 mass % (5.5 to 11.34 mass % in terms of a solid content). For example, in Nikasol TS-620, the aqueous emulsion contains 55 to 63% of poly(methyl acrylate/2-ethylhexyl acrylate) in terms of a solid content. When a gel patch is produced using the aqueous emulsion of the polymer, the content of water in the above paste layer also includes the amount of water added as a medium for the aqueous emulsion.

Other drugs, a plant-derived component, an animal-derived component, a water-soluble polymer, a dissolution aid, a cross-linking agent, a moisturizing agent, a refreshing agent, a stabilizer, an inorganic powder, a colorant, a fragrance agent, a pH adjusting agent and the like may be added as other components to the paste layer.

The other drug is a physiologically active substance other than ketoprofen and may be any drug having percutaneous absorption. Examples of other drugs include non-steroidal anti-inflammatory drugs such as felbinac, flurbiprofen, diclofenac, diclofenac sodium, methyl salicylate, glycol salicylate, indometacin, and ketoprofen or esters thereof, antihistamines such as diphenhydramine, painkillers such as aspirin, acetaminophen, ibuprofen, and loxoprofen sodium, local anesthetics such as lidocaine, muscle relaxants such as suxamethonium chloride, antifungal agents such as clotrimazole, antihypertensive drugs such as clonidine, vasodilators such as nitroglycerin, and isosorbide dinitrate, vitamins such as vitamin A, vitamin E (tocopherol), tocopherol acetate, vitamin K, octothiamine, and riboflavin butyrate, prostaglandins, scopolamine, fentanyl, l-menthol, capsicum extracts, and nonylic acid vanillyl amides. In some physiologically active substances, there are two types of optical isomers: R-form and S-form. The physiologically active substance used in the present embodiment may be any one optical isomer or may be a mixture containing two types of optical isomers at an arbitrary ratio.

Examples of pharmaceutically acceptable salts of physiologically active substances include inorganic salts such as sodium salts, potassium salts, and calcium salts; and amine salts such as monoethanolamine and diethanolamine.

The plant-derived component may be a component extracted from at least a part of the plant (for example, leaves, roots, skins, and fruits) or a hydrolysate thereof, and examples thereof include fruit-derived components such as rose fruit extracts, orange extracts, orange juice, raspberry extracts, kiwi extracts, cucumber extracts, *gardenia* extracts, grapefruit extracts, hawthorn extracts, Japanese pepper extracts, white thorn extracts, *juniper* extracts, jujube extracts, Langsat/Duku extracts, tomato extracts, grape extracts, loofah extracts, lime juice, apple extracts, apple juice, lemon extracts, and lemon juice, and components extracted from various crude drugs such as allantoin, lecithin, amino acids, kojic acid, aloe and licorice. In addition, examples of plant-derived components include *angelica* extracts, *avocado* extracts, sweet *hydrangea* leaf extracts, *althea* extracts, *arnica* extracts, *ginkgo* extracts, fennel extracts, turmeric extracts, oolong tea extracts, *scutellaria* root extracts, cork tree bark extracts, barley extracts, watercress extracts, seaweed extracts, hydrolyzed elastin, hydrolyzed wheat powder, *chamomilla recutita* extracts, capillary *Artemisia* extracts, licorice extracts, karkade extracts, guanosine, kuma bamboo grass extracts, walnut extracts, *clematis* extracts, burdock extracts, comfrey extracts, lingonberry extracts, *bupleurum* root extracts, *salvia* extracts, soapwort extracts, bamboo grass extracts, hawthorn extracts, shiitake extracts, *rehmannia* root extracts, *lithospermum* root extracts, linden extracts, *filipendula* extracts, *acorus calamus* extracts, white birch extracts, horsetail extracts, honeysuckle extracts, ivy extracts, white thorn extracts, *sambucus nigra* extracts, yarrow extracts, *mentha piperita* extracts, mallow extracts, *swertia japonica* extracts, jujube extracts, thyme extracts, clove extracts, cogongrass extracts, *citrus unshiu* peel extracts, spruce extracts, *houttuynia cordata* extracts, *bacillus natto* extracts, *ginseng* extracts, wild rose extracts, hibiscus extracts, *ophiopogon* root extracts, parsley extracts, pellitory extracts, *isodon japonicus* extracts, bisabolol, coltsfoot extracts, Japanese butterbur extracts, poria extracts, butcher's broom extracts, propolis, peppermint extracts, *tilia miqueliana* extracts, hop extracts, pine extracts, horse chestnut extracts, skunk cabbage extracts, mukurossi extracts, peach leaf extracts, cornflower extracts, *eucalyptus* extracts, *citrus* extracts, mugwort extracts, lavender extracts, lettuce extracts, *astragalus sinicus* extracts, rose extracts, rosemary extracts, and roman chamomile extracts.

The animal-derived component may be a component extracted from at least a part of the animal (for example, placenta, and umbilical cord) or a hydrolysate thereof, or may be component produced by the animal, and examples thereof include placenta extracts, umbilical cord extracts, water-soluble placenta extracts, hydrolyzed silk, honey, royal jelly extracts, and yeast extracts.

The water-soluble polymer is not particularly limited as long as it can retain water in the gel patch, and those generally known to those skilled in the art can be used. Examples of water-soluble polymers include gelatin, polyvinyl alcohol, polyvinylpyrrolidone, sodium alginate, hydroxypropyl cellulose, sodium carboxymethyl cellulose (carmelose sodium), methyl cellulose, and carrageenan, and these may be used alone or two or more thereof may be used in combination. The water-soluble polymer is preferably carmelose sodium, gelatin or polyvinyl alcohol. The content of the water-soluble polymer based on a mass of the paste layer is preferably 3 to 10 mass %.

The dissolution aid is not particularly limited as long as it can dissolve the drug, and examples thereof include crotamiton; N-methylpyrrolidone; polyalkylene glycols such as polyethylene glycol (PEG), and polybutylene glycol; oxyalkylene fatty acid esters such as polyethylene glycol monostearate; polyoxyalkylene sorbitan fatty acid esters such as polysorbate 80; and surfactants such as polyoxyethylene hydrogenated castor oil. These dissolution aids may be used alone or two or more thereof may be used in combination. The content of the dissolution aid based on a mass of the paste layer is preferably 0.1 to 10 mass %.

The cross-linking agent is a component for adjusting the degree of progress of a crosslinking reaction between neutralized polyacrylic acids and a crosslinking reaction between the neutralized polyacrylic acid and polyacrylic acid that is optionally added, and those generally used in the art can be used. Examples of cross-linking agents include an aluminum compound. The content of the cross-linking agent based on a mass of the paste layer is preferably 0.01 to 6 mass %. When the content of the cross-linking agent is within the above range, a gel patch having better followability to the skin can be obtained.

The moisturizing agent is not particularly limited as long as it can minimize evaporation of water from the paste layer over time. Examples of moisturizing agents include polyhydric alcohols such as concentrated glycerin, sorbitol, ethylene glycol, 1,4-butanediol, polyethylene glycol, and liquid paraffin. These moisturizing agents may be used alone or two or more thereof may be used in combination. The moisturizing agent is preferably concentrated glycerin. The content of the moisturizing agent based on a mass of the paste layer is preferably 20 to 40 mass %.

Examples of refreshing agents include thymol, 1-menthol, dl-menthol, 1-isopulegol, and mint oil. A preferable refreshing agent is 1-menthol. The content of the refreshing agent based on a total mass of the paste layer is preferably 0.5 to 3 mass %. In addition, the content of 1-menthol based on a total mass of the paste layer is preferably 0.1 to 0.5 mass % and more preferably 0.2 to 0.4 mass %. When the content of 1-menthol is 0.1 mass % or more, a sufficient cooling feeling can be provided for a user of the gel patch. In addition, when the content of 1-menthol is 0.5 mass % or less, the storage stability with respect to ketoprofen becomes better.

Examples of stabilizers include oxybenzone, dibutylhydroxytoluene (BHT), sodium edetate, and a UV absorber (for example, dibenzoyl methane derivative). The content of the stabilizer based on a mass of the paste layer is preferably 0.5 to 3 mass %.

The mass of the paste layer may be 214 to 1,000 $g/m^2$, 400 to 1,000 $g/m^2$, or 400 to 650 $g/m^2$. Preferably, when the mass is 400 to 650 $g/m^2$, a fitting feeling becomes favorable, and the adhesiveness for a longer period can be improved. When the mass of the paste layer is within the above range, the thickness of the entire gel patch can be reduced, it can easily follow the skin, and moreover, since the step between peripheral portions when applied becomes small, it tends to be unlikely to peel off.

The pH of the paste layer is preferably 4 to 8 and more preferably 4.5 to 6. When the pH is 4 or more, there is little skin irritation and when the pH is 8 or less, the moldability and shape retention of the gel patch can be improved. In particular, when the support is a woven fabric, and particularly a knitted fabric, exudation may occur when the paste layer is formed, but when the pH is 5 to 6.5, exudation tends to be minimized. Here, for example, the pH can be measured by diluting a sample in purified water by a factor of 20 using a glass composite electrode according to the pH measurement method of Japanese Pharmacopoeia general test method.

The gel patch may have a release liner. The release liner is laminated on the surface opposite to the support with respect to the paste layer. When the release liner is provided, during storage, it is possible to minimize a decrease in the water content of the paste layer and there is a tendency for reducing adhesion of dust and the like to the paste layer.

The material of the release liner is not particularly limited, and a liner made of a material generally known to those skilled in the art can be used. When a woven fabric, a non-woven fabric, a knitted fabric or a resin film is used as the support, examples of materials of the release liner include polyethylene, polypropylene, polybutylene, polyethylene terephthalate, rayon, and polyurethane, and these may be used alone or two or more thereof may be used in combination. The material of the release liner is preferably a polypropylene film.

The gel patch may be stored in a pouch. When the gel patch is stored in the pouch, it is possible to minimize a decrease in the water content of the paste layer, and it is possible to reduce adhesion of dust and the like to the paste layer.

The gel patch can be produced, for example, by mixing ketoprofen, propylene glycol, and water, adding the above optional components to obtain a paste solution, uniformly spreading the paste solution on a release liner, and laminating a support thereon.

An aspect of the present invention also provides a method of stabilizing ketoprofen in a gel patch having a paste layer containing ketoprofen or a pharmaceutically acceptable salt thereof on a support, including incorporating a mass of propylene glycol 3 times the mass of ketoprofen or less into the paste layer.

A second embodiment of the present invention is a gel patch having a paste layer on a support, and additionally having a release liner on the side opposite to the support with respect to the paste layer, and in which the paste layer contains a physiologically active substance, water, at least one of poly(methyl acrylate/2-ethylhexyl acrylate) and poly(methacrylic acid/n-butyl acrylate), and at least one of a fatty acid alkyl ester and an alkylene dicarboxylic acid ester, and the loss modulus of the paste layer after being left under an environment of a temperature of 25° C. and a relative humidity of 55% for 24 hours after the release liner is peeled off is 3,000 to 7,000 Pa under conditions of a frequency of 15 Hz and a measurement temperature of 32° C.

The inventors found that, after a gel patch containing poly(methyl acrylate/2-ethylhexyl acrylate) is applied for one day, the peel strength of the paste layer increases and pain may occur during peeling off. The inventors conducted additional studies and as a result, found that, when a fatty acid alkyl ester or a dicarboxylic acid ester is added to a gel patch containing poly(methyl acrylate/2-ethylhexyl acrylate), the increase of the peel strength can be reduced without impairing the adhesion strength. The inventors thought that, when a fatty acid alkyl ester or an alkylene dicarboxylic acid ester is added to a gel patch containing poly(methyl acrylate/2-ethylhexyl acrylate) or poly(methacrylic acid/n-butyl acrylate), the loss modulus (G") in the high frequency range (particularly 15 Hz) of the paste layer becomes a predetermined value, and the increase of the peel strength can be reduced.

Regarding the support of the gel patch according to the present embodiment, those described in the first embodiment can be used.

The paste layer of the gel patch according to the present embodiment contains a physiologically active substance, water, at least one of poly(methyl acrylate/2-ethylhexyl acrylate) and poly(methacrylic acid/n-butyl acrylate), and at least one of a fatty acid alkyl ester and an alkylene dicarboxylic acid ester.

The physiologically active substance is not limited to ketoprofen or a pharmaceutically acceptable salt thereof, and may be any substance having percutaneous absorption. Regarding the physiologically active substance used in the present embodiment, ketoprofen or a pharmaceutically acceptable salt thereof described in the first embodiment and other physiologically active substances can be used. Physiologically active substances may be used alone or two or more thereof may be used in a mixture. A preferable physiologically active substance is ketoprofen.

The content of the physiologically active substance in the paste layer based on a mass of the entire paste layer is 1.5 to 2.5 mass % and preferably 1.8 to 2.2 mass %. Here, when the paste layer contains a pharmaceutically acceptable salt of a physiologically active substance, a content proportion of each component is calculated by converting the mass of the salt into mass of the physiologically active substance (free form).

The content of water in the paste layer based on a total mass of the paste layer may be 30 to 60 mass % or 35 to 50 mass %.

Regarding poly(methyl acrylate/2-ethylhexyl acrylate) or poly(methacrylic acid/n-butyl acrylate), those described in the first embodiment can be used.

A total content of poly(methyl acrylate/2-ethylhexyl acrylate) and poly(methacrylic acid/n-butyl acrylate) based on a total mass of the paste layer may be 2.75 to 15.75 mass % and is preferably 3.3 to 13.86 mass %, 5.5 to 12.6 mass % or 5.5 to 11.34 mass % in terms of a solid content.

A total content of the aqueous emulsion of poly(methyl acrylate/2-ethylhexyl acrylate) and poly(methacrylic acid/n-butyl acrylate) based on a total mass of the paste layer may be 5 to 25 mass % (2.75 to 15.75 mass % in terms of a solid content), and is preferably 6 to 22 mass % (3.3 to 13.86 mass % in terms of a solid content), 10 to 20 mass % (5.5 to 12.6 mass % in terms of a solid content) or 10 to 18 mass % (5.5 to 11.34 mass % in terms of a solid content). For example, in Nikasol TS-620, the aqueous emulsion contains 55 to 63% of poly(methyl acrylate/2-ethylhexyl acrylate) in terms of a solid content. When a gel patch is produced using the aqueous emulsion of the polymer, the content of water in the above paste layer also includes the amount of water added as a medium for the aqueous emulsion.

Regarding the fatty acid alkyl ester and the alkylene dicarboxylic acid ester, those described in the first embodiment can be used.

The content of the fatty acid alkyl ester based on a total mass of the paste layer may be 1 to 20 mass % and is preferably 1 to 15 mass % or 2 to 13 mass %. In particular, the content of hexyl laurate based on a total mass of the paste layer may be 0.5 to 10 mass % and is preferably 0.5 to 5.0 mass % or 1.0 to 3.5 mass %. When the content of hexyl laurate, isopropyl myristate or isopropyl palmitate is 0.5 to 5.0 mass %, the loss modulus can be easily adjusted to within a predetermined range, and the skin permeability of the physiologically active substance is particularly excellent.

The content of the alkylene dicarboxylic acid ester based on a total mass of the paste layer may be 1 to 20 mass %, and is preferably 1 to 15 mass % or 2 to 13 mass %. In particular, the content of the diisopropyl adipate based on a total mass of the paste layer may be 0.5 to 10 mass % and is preferably 0.5 to 5.0 mass % or 1.0 to 3.5 mass %. When the content of the diisopropyl adipate is 0.5 to 5.0 mass %, the loss modulus can be easily adjusted to within a predetermined range, and the skin permeability of the physiologically active substance is particularly excellent.

A total content of the fatty acid alkyl ester and the alkylene dicarboxylic acid ester based on a total mass of the paste layer may be 1 to 10 mass %.

The paste layer may further contain propylene glycol. Propylene glycol has an excellent effect of improving the skin permeability of the physiologically active substance. In particular, when the physiologically active substance is ketoprofen, an effect of improving the skin permeability with propylene glycol is more significant.

The content of propylene glycol in the paste layer based on a mass is 3-fold or less and may be 0.5 to 3-fold, 0.7 to 3-fold, 1 to 3-fold, 0.5 to 2.5-fold, 0.7 to 2.5-fold, 1 to 2.5-fold, or 1.5 to 2.5-fold the content of the physiologically active substance.

The paste layer may further contain a neutralized polyacrylic acid. The neutralized polyacrylic acid may be a completely neutralized polyacrylic acid, a partially neutralized polyacrylic acid, or a mixture thereof. Examples of neutralized polyacrylic acids include polyacrylate, and for example, sodium salts, potassium salts, calcium salts, and ammonium salts can be used.

The neutralized polyacrylic acid is preferably a partially neutralized polyacrylic acid because an initial adhesion strength and an adhesion strength over time are strong. The partially neutralized polyacrylic acid is one in which there are a structural unit derived from an acrylic acid and a structural unit derived from an acrylate at an arbitrary ratio in one polymer chain. Regarding the partially neutralized polyacrylic acid, one in which 50 mol % of carboxyl groups in one polymer chain are neutralized is preferably used.

The content of the neutralized polyacrylic acid in the paste layer based on a total mass of the paste layer is preferably 1 to 6 mass % and more preferably 2 to 6 mass %. When the content of the neutralized polyacrylic acid is 1 mass % or more, the adhesion strength of the paste layer is sufficiently high and it becomes unlikely to fall off. When the content of the neutralized polyacrylic acid is 6 mass % or less, the moldability and shape retention of the paste layer are improved.

The paste layer may further contain polyacrylic acid. When polyacrylic acid is contained, the maintenance performance of the adhesion strength is kept high and the shape retention of the gel patch is improved. The content of polyacrylic acid based on a mass of the paste layer is preferably 1 to 5 mass %. When the content of polyacrylic acid is 1 mass % or more, the moldability and shape retention of the paste layer are improved. When the content of polyacrylic acid is 5 mass % or less, the hardness of the paste layer is less likely to increase and the adhesion to the skin increases. When both the neutralized polyacrylic acid and polyacrylic acid are contained, the stickiness, moldability, shape retention and hardness of the gel patch are improved in a well-balanced manner.

A plant-derived component, an animal-derived component, a water-soluble polymer, a dissolution aid, a cross-linking agent, a moisturizing agent, a refreshing agent, a stabilizer, an inorganic powder, a colorant, a fragrance agent, a pH adjusting agent and the like may be added as other component to the paste layer. Regarding these components, those described in the first embodiment can be used.

The mass of the paste layer may be 214 to 1,000 g/m$^2$, 400 to 1,000 g/m$^2$, or 400 to 650 g/m$^2$. Preferably, when the mass is 400 to 650 g/m$^2$, a fitting feeling becomes favorable, and the adhesiveness for a longer period can be improved. When the mass of the paste layer is within the above range, the thickness of the entire gel patch can be reduced, it can easily follow to the skin, and moreover, since the step between peripheral portions when applied becomes small, it tends to be unlikely to peel off.

The pH of the paste layer is preferably 4 to 8 and more preferably 4.5 to 6. When the pH is 4 or more, there is little skin irritation and when the pH is 8 or less, the moldability and shape retention of the gel patch can be improved. In particular, when the support is a woven fabric, and particularly a knitted fabric, exudation may occur when the paste layer is formed, but when the pH is 5 to 6.5, exudation tends to be minimized. Here, for example, the pH can be measured by diluting a sample in purified water by a factor of 20 using a glass composite electrode according to the pH measurement method of Japanese Pharmacopoeia general test method.

The gel patch has a release liner on the side opposite to the support with respect to the paste layer. When the release liner is provided, during storage, it is possible to minimize a decrease in the water content of the paste layer and there is a tendency for reducing adhesion of dust and the like to the paste layer.

The material of the release liner is not particularly limited, and a liner made of a material generally known to those skilled in the art can be used. When a woven fabric, a non-woven fabric, a knitted fabric or a resin film is used as the support, examples of materials of the release liner include polyethylene, polypropylene, polybutylene, polyethylene terephthalate, rayon, and polyurethane, and these may be used alone or two or more thereof may be used in combination. The material of the release liner is preferably a polypropylene film.

The gel patch may be stored in a pouch. When the gel patch is stored in the pouch, it is possible to minimize a decrease in the water content of the paste layer, and it is possible to reduce adhesion of dust and the like to the paste layer.

The gel patch can be produced by, for example, mixing a physiologically active substance, water, at least one of poly(methyl acrylate/2-ethylhexyl acrylate) and poly(methacrylic acid/n-butyl acrylate), and at least one of a fatty acid alkyl ester and an alkylene dicarboxylic acid ester, adding the above optional component to obtain a paste solution, uniformly spreading the paste solution on a release liner, and laminating a support thereon.

After the gel patch according to the present embodiment is left under an environment of a temperature of 25° C. and a relative humidity of 55% for 24 hours after the release liner is peeled off, when a viscoelasticity test is performed under conditions of a frequency of 15 Hz and a measurement temperature of 32° C., the loss modulus of the paste layer is 3,000 to 7,000 Pa and preferably 5,000 to 7,000 Pa. The gel patch can be produced by laminating the release liner after the paste solution spreads on the support. In addition, the gel patch may be produced by spreading the paste solution on the release liner and laminating the support. The loss modulus is preferably a numerical value measured after being left under an environment of a temperature of 25° C. and a relative humidity of 55% for 24 hours after the gel patch is produced by the method and the release liner is then peeled off.

EXAMPLES

While the present invention will be described below in more detail with reference to examples and test examples, the present invention is not limited to these examples. In addition, the numbers shown in Table 1, Table 3 and Table 5 represent mass % unless otherwise specified.

Examples 1 to 4 and Comparative Examples 1 to 6

(1) Production of Gel Patch

Respective components shown in Table 1 were mixed for a certain time to obtain a paste solution. The obtained paste solution was uniformly spread on a release liner so that the paste mass per gel patch sheet (140 mm×100 mm) was 6 g, and a knitted fabric (support) was then immediately laminated to produce a gel patch.

TABLE 1

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Ketoprofen | 2 | 2 | 2 | 2 | 2 | 2 |
| l-menthol | 0.3 | 0.3 | 0.3 | 0.3 | 0.3 | 0.3 |
| Gelatin | 2.5 | 2.5 | 2.5 | 2.5 | 3.5 | 2.5 |
| Partially neutralized polyacrylic acid | 5 | 6 | 6 | 5 | 5 | 5 |
| Polyvinyl alcohol | 2.5 | 2.5 | 2.5 | 2.5 | 2.5 | 3.5 |
| Polyacrylic acid | 1.5 | 2 | 2 | 1.5 | 1.5 | 1.5 |
| Concentrated glycerin | 15 | 15 | 15 | 15 | 15 | 15 |
| Propylene glycol | 15 | 10 | 7.5 | 7.5 | 7.5 | 7.5 |
| Nikasol TS-620 | 16.67 | 12.5 | 12.5 | 12.5 | 12.5 | 12.5 |
| Hexyl laurate | 0 | 0 | 0 | 0 | 0 | 0 |
| Purified water | 33.275 | 40.945 | 43.445 | 44.945 | 43.945 | 43.945 |
| Other components | 6.255 | 6.255 | 6.255 | 6.255 | 6.255 | 6.255 |
| Total | 100 | 100 | 100 | 100 | 100 | 100 |

|  | Ex. 1 | Ex. 2 | Ex. 3 | Ex. 4 |
|---|---|---|---|---|
| Ketoprofen | 2 | 2 | 2 | 2 |
| l-menthol | 0.3 | 0.3 | 0.3 | 0.3 |
| Gelatin | 2.5 | 2.5 | 2.5 | 2.5 |
| Partially neutralized polyacrylic acid | 5 | 5 | 6 | 6 |
| Polyvinyl alcohol | 2.5 | 2.5 | 2.5 | 2.5 |
| Polyacrylic acid | 2.5 | 1.5 | 2 | 2 |
| Concentrated glycerin | 15 | 18.5 | 15 | 15 |
| Propylene glycol | 5 | 5 | 5 | 5 |
| Nikasol TS-620 | 12.5 | 12.5 | 12.5 | 12.5 |
| Hexyl laurate | 0 | 0 | 2.5 | 3.5 |
| Purified water | 46.445 | 43.945 | 43.445 | 42.445 |
| Other components | 6.255 | 6.255 | 6.255 | 6.255 |
| Total | 100 | 100 | 100 | 100 |

(2) Evaluation of Storage Stability

The obtained gel patch was stored at 60° C. for 2 weeks. The gel patch after storage was cut so that the application area was 35 cm² (5 cm×7 cm), the release liner was then removed, and the paste layer was extracted in 30 mL of methanol to obtain a sample solution. The content of ketoprofen and a total content of ketoprofen esters (glyceryl, propylene glycolyl, menthyl, or ethylhexyl esters of ketoprofen) in the sample solution were calculated based on the peak area by a high performance liquid chromatography (HPLC) method.

The results are shown in Table 2. A total amount of ketoprofen esters was calculated as a relative value (mol %) when the amount of ketoprofen during gel patch production was 100. The amounts of ketoprofen in the respective examples were 95% or more based on the content of ketoprofen during gel patch production. On the other hand, the amount of ketoprofen esters was 2.2% or more in Comparative Examples 1 to 6, but less than 2.1% in Examples 1 to 4. In the gel patches containing hexyl laurate of Example 3 and Example 4, the total amount of esters was further reduced.

TABLE 2

|  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|
| Total amount of esters [%] | 3.53 | 2.77 | 2.37 | 2.25 | 2.33 | 2.25 |

|  | Example 1 | Example 2 | Example 3 | Example 4 |
|---|---|---|---|---|
| Total amount of esters [%] | 1.87 | 2.01 | 1.62 | 1.49 |

Examples 5 to 10 and Comparative Examples 7 to 13

(1) Production of Gel Patch

Respective components shown in Table 3 were mixed for a certain time to obtain a paste solution. The obtained paste solution was uniformly spread on a release liner so that the paste mass per gel patch sheet (140 mm×100 mm) was 6 g, and a knitted fabric (support) was then immediately laminated to produce a gel patch.

(2) Evaluation of Storage Stability

According to the above method, the content of ketoprofen and a total content of ketoprofen esters in the sample solution were calculated based on the peak area by a high performance liquid chromatography (HPLC) method.

The results are shown in Table 4. The amounts of ketoprofen in the respective examples were 95% or more based on the content of ketoprofen during gel patch production. On the other hand, the amount of ketoprofen esters was 2.29% or more in Comparative Examples 7 and 13, but less than 2.1% in Examples 5 to 10.

TABLE 3

|  | Comp. Ex. 7 | Comp. Ex. 8 | Comp. Ex. 9 | Comp. Ex. 10 | Comp. Ex. 11 | Comp. Ex. 12 | Comp. Ex. 13 |
| --- | --- | --- | --- | --- | --- | --- | --- |
| Ketoprofen | 2 | 2 | 2 | 2 | 2 | 2 | 2 |
| 1-menthol | 0.3 | 0.3 | 0.3 | 0.3 | 0.3 | 0.3 | 0.3 |
| Gelatin | 2.5 | 2.5 | 2.5 | 2.5 | 2.5 | 2.5 | 2.5 |
| Partially neutralized polyacrylic acid | 5.5 | 6 | 6 | 6 | 5 | 5 | 5 |
| Polyvinyl alcohol | 2.5 | 2.5 | 2.5 | 2.5 | 2.5 | 3.5 | 2.5 |
| Polyacrylic acid | 2 | 2 | 2 | 2 | 2 | 1.5 | 1.5 |
| Concentrated glycerin | 20 | 20 | 20 | 20 | 20 | 20 | 20 |
| Propylene glycol | 7.5 | 7.5 | 7.5 | 7.5 | 7.5 | 7.5 | 6.5 |
| Nikasol TS-620 | 12.5 | 12.5 | 12.5 | 12.5 | 12.5 | 12.5 | 12.5 |
| Hexyl laurate | 0 | 0 | 1 | 1.5 | 1.5 | 1.5 | 0 |
| Purified water | 38.945 | 37.445 | 37.445 | 36.945 | 37.945 | 38.445 | 40.945 |
| Other components | 6.255 | 7.255 | 6.255 | 6.255 | 6.255 | 6.255 | 6.255 |
| Total | 100 | 100 | 100 | 100 | 100 | 100 | 100 |

|  | Ex. 5 | Ex. 6 | Ex. 7 | Ex. 8 | Ex. 9 | Ex. 10 |
| --- | --- | --- | --- | --- | --- | --- |
| Ketoprofen | 2 | 2 | 2 | 2 | 2 | 2 |
| 1-menthol | 0.3 | 0.3 | 0.3 | 0.3 | 0.3 | 0.3 |
| Gelatin | 2.5 | 2.5 | 2.5 | 2.5 | 2.5 | 2.5 |
| Partially neutralized polyacrylic acid | 6 | 5 | 5 | 6 | 5 | 5 |
| Polyvinyl alcohol | 2.5 | 2.5 | 2.5 | 2.5 | 2.5 | 2.5 |
| Polyacrylic acid | 2 | 1.5 | 2 | 2 | 1.5 | 1.5 |
| Concentrated glycerin | 20 | 20 | 20 | 20 | 20 | 20 |
| Propylene glycol | 5 | 5 | 5 | 5 | 5 | 2 |
| Nikasol TS-620 | 12.5 | 12.5 | 12.5 | 12.5 | 12.5 | 12.5 |
| Hexyl laurate | 2.5 | 2.5 | 2.5 | 3.5 | 13 | 2.5 |
| Purified water | 38.445 | 39.945 | 39.445 | 37.445 | 29.445 | 42.945 |
| Other components | 6.255 | 6.255 | 6.255 | 6.255 | 6.255 | 6.255 |
| Total | 100 | 100 | 100 | 100 | 100 | 100 |

TABLE 4

|  | Comp. Ex. 7 | Comp. Ex. 8 | Comp. Ex. 9 | Comp. Ex. 10 | Comp. Ex. 11 | Comp. Ex. 12 | Comp. Ex. 13 |
|---|---|---|---|---|---|---|---|
| Total amount of esters [%] | 2.29 | 2.37 | 2.47 | 2.51 | 2.58 | 2.43 | 2.47 |

|  | Ex. 5 | Ex. 6 | Ex. 7 | Ex. 8 | Ex. 9 | Ex. 10 |
|---|---|---|---|---|---|---|
| Total amount of esters [%] | 2.01 | 1.82 | 1.86 | 1.84 | 1.95 | 1.53 |

Example 11 and Comparative Examples 14 and 15

(1) Production of Gel Patch

Respective components shown in Table 5 were mixed for a certain time to obtain a paste solution. The obtained paste solution was uniformly spread on a release liner so that the paste mass per gel patch sheet (140 mm×100 mm) was 6 g, and a knitted fabric (support) was then immediately laminated to produce a gel patch.

TABLE 5

|  | Ex. 6 | Comp. Ex. 14 | Comp. Ex. 15 | Ex. 11 |
|---|---|---|---|---|
| Ketoprofen | 2 | 2 | 2 | 2 |
| l-menthol | 0.3 | 0.7 | 1 | 0.3 |
| Gelatin | 2.5 | 2.5 | 2.5 | 2.5 |
| Partially neutralized polyacrylic acid | 5 | 5 | 5 | 5 |
| Polyvinyl alcohol | 2.5 | 2.5 | 2.5 | 2.5 |
| Polyacrylic acid | 1.5 | 1.5 | 1.5 | 1.5 |
| Concentrated glycerin | 20 | 20 | 20 | 20 |
| Propylene glycol | 5 | 5 | 5 | 5 |
| Nikasol TS-620 | 12.5 | 12.5 | 12.5 | 12.5 |
| Hexyl laurate | 2.5 | 2.5 | 2.5 | — |
| Isopropyl myristate | — | — | — | 2.5 |
| Purified water | 39.945 | 39.545 | 39.245 | 39.945 |
| Other components | 6.255 | 6.255 | 6.255 | 6.255 |
| Total | 100 | 100 | 100 | 100 |

(2) Evaluation of Storage Stability

According to the above method, the content of ketoprofen and a total content of ketoprofen esters in the sample solution were calculated based on the peak area by a high performance liquid chromatography (HPLC) method.

The results are shown in Table 6. The total amount of ketoprofen esters was 2.5% or more in Comparative Examples 14 and 15, and 2% or less in Example 11.

TABLE 6

|  | Ex. 6 | Comp. Ex. 14 | Comp. Ex. 15 | Ex. 11 |
|---|---|---|---|---|
| Total amount of esters [%] | 1.82 | 2.59 | 2.52 | 2.00 |

Reference Examples 1 to 7

(1) Production of Gel Patch

Respective components shown in Table 7 were mixed for a certain time to obtain a paste solution. The obtained paste solution was uniformly spread on a release liner so that the paste mass per gel patch sheet (140 mm×100 mm) was 6 g, and a knitted fabric (support) was then immediately laminated to produce a gel patch.

TABLE 7

|  | Ref. Ex. 1 | Ref. Ex. 2 | Ref. Ex. 3 | Ref. Ex. 4 | Ref. Ex. 5 | Ref. Ex. 6 | Ref. Ex. 7 |
|---|---|---|---|---|---|---|---|
| Ketoprofen | 2.0 | 2.0 | 2.0 | 2.0 | 2.0 | 2.0 | 2.0 |
| L-menthol | 0.3 | 0.3 | 0.3 | 0.3 | 0.3 | 0.3 | 0.3 |
| Gelatin | 2.5 | 2.5 | 2.5 | 2.5 | 2.5 | 2.5 | 2.5 |
| Partially neutralized polyacrylic acid | 5.0 | 5.0 | 5.0 | 5.0 | 5.0 | 5.0 | 5.0 |
| Polyvinyl alcohol | 2.5 | 2.5 | 2.5 | 2.5 | 2.5 | 2.5 | 2.5 |
| Polyacrylic acid | 1.5 | 1.5 | 1.5 | 1.5 | 1.5 | 1.5 | 1.5 |
| Glycerin | 15.0 | 18.5 | 20.0 | 20.0 | 20.0 | 20.0 | 20.0 |
| Propylene glycol | 15.0 | 5.0 | 5.0 | 7.5 | 5.0 | 5.0 | 5.0 |
| Nikasol TS-620 | 16.7 | 12.5 | 12.5 | 12.5 | 12.5 | 12.5 | 12.5 |
| Hexyl laurate | — | — | 2.5 | 1.5 | — | — | — |

TABLE 7-continued

|  | Ref. Ex. 1 | Ref. Ex. 2 | Ref. Ex. 3 | Ref. Ex. 4 | Ref. Ex. 5 | Ref. Ex. 6 | Ref. Ex. 7 |
|---|---|---|---|---|---|---|---|
| Isopropyl myristate | — | — | — | — | 2.5 | — | — |
| Isopropyl palmitate | — | — | — | — | — | 2.5 | — |
| Diisopropyl adipate | — | — | — | — | — | — | 2.5 |
| Other components | 6.255 | 6.255 | 6.255 | 6.255 | 6.255 | 6.255 | 6.255 |
| Purified water | 33.275 | 43.945 | 39.945 | 38.445 | 39.945 | 39.945 | 39.945 |
| Total | 100 | 100 | 100 | 100 | 100 | 100 | 100 |

(2) Evaluation

Test 1: Probe Tack Test

The release liner was removed from each gel patch, and the probe tack was evaluated under the following test conditions. In addition, assuming the adhesion strength 24 hours after application to the skin, the produced gel patch from which the release liner was removed was left under conditions of a temperature of 25° C. and a relative humidity of 55% for 24 hours, and the probe tack test was then performed similarly.

[Test Conditions]
Device: probe tack tester (commercially available from Tester Sangyo Co., Ltd.)
Probe: bakelite probe
Contact speed: 1 cm/sec
Contact time: 1 second
Retaining ring: 20 g, made of brass Test 2: Ball Tack Test The release liner was removed from each gel patch (size: 50 mm×100 mm), and the ball tack test was performed according to the method described in JIS Z0237: 2009. The gel patch was arranged on an inclined plate of a ball rolling device so that the paste surface (surface to be applied to the skin) of the gel patch was the upper surface. The tilt angle of the inclined plate was 30°. When a ball having a predetermined diameter was arranged at a position (start position) of 100 mm (runway) from the upper end (upper side) of the paste layer, it was evaluated whether the ball rolled on the inclined plate and remained on the paste layer for 5 seconds or longer. There were 32 types of balls to be arranged with sizes that increased by 1/32 of an inch from a ball having a diameter of 1/32 of an inch, and the diameter of the largest ball was 1 inch (32/32 of an inch). Among the balls that stopped without passing over the paste layer, the diameter of the ball having the largest diameter was recorded.

Test 3: 180° Peel Strength Test

The produced gel patch was cut into a rectangle so that the width was 2.5 cm and applied to a test plate. The gel patch was pressed with a roller and then peeled off at a constant speed under the following test conditions. A load (peel strength) required for peeling off the gel patch was measured.

In addition, in order to estimate the degree of pain in peeling off 24 hours after application to the skin, when the release liner was removed from the produced gel patch, and pressing was performed with a roller on a test plate, after being left under conditions of a temperature of 25° C. and a relative humidity of 55% for 24 hours, a 180° peel strength test was performed similarly.

[Test Conditions]
Device: tensilon type tensile tester (product name: RTA-100, commercially available from A&D Co., Ltd.)
Test plate: PTFE plate
Peeling rate: 300 mm/min Test 4: Viscoelasticity Test Assuming the adhesion strength 24 hours after application to the skin, the produced gel patch from which the release liner was removed was left under conditions of a temperature of 25° C. and a relative humidity of 55% for 24 hours, and the loss modulus was then measured under the following measurement conditions. Among the obtained loss moduli, the loss modulus at a frequency of 15 Hz was recorded.

[Measurement Conditions]
Device: Rheometer HAAKE MARS-III (commercially available from Thermo Fisher Scientific)
Sample part: parallel plate having a diameter of 20 mm
Gap interval: 1 mm
Sample amount: 0.7 g
Temperature: 32° C.
Frequency: 0.01 to 100 Hz
Strain: 1%

The results are shown in Table 8. Compared with the gel patches of Reference Examples 1 and 2, in the gel patches of Reference Examples 3 to 7, the increase in the peel strength was significantly reduced even after being left for 24 hours. On the other hand, regarding the probe tack value, no significant difference was observed between Reference Examples 1 and 2 and Reference Examples 3 to 7, and the adhesion strength was maintained. In Reference Example 1, in a range of 0.1 to 100 Hz, the value of the loss tangent (tan δ) was higher than that of other gel patches. In Reference Example 2, in a range of 0.01 to 100 Hz, the storage modulus (G') was larger than that of other gel patches.

TABLE 8

|  |  | Ref. Ex. 1 | Ref. Ex. 2 | Ref. Ex. 3 | Ref. Ex. 4 |
|---|---|---|---|---|---|
| Immediately after production | Probe tack [N] | 0.23 | 0.32 | 0.26 | 0.23 |
|  | Ball tack [inch] | 10/32 | 12/32 | 10/32 | 11/32 |
|  | Peel strength [N] | 0.045 | 0.06 | 0.019 | 0.026 |
| After 24 hours | Probe tack [N] | 0.52 | 0.67 | 0.68 | 0.60 |
|  | Peel strength [N] | 0.41 | 0.42 | 0.09 | 0.07 |
|  | Loss modulus [Pa] | 7,349 | 8,258 | 5,620 | 6,621 |

TABLE 8-continued

|  |  | Ref. Ex. 5 | Ref. Ex. 6 | Ref. Ex. 7 |
|---|---|---|---|---|
| Immediately after production | Probe tack [N] | 0.29 | 0.27 | 0.27 |
|  | Ball tack [inch] | 10/32 | 10/32 | 10/32 |
|  | Peel strength [N] | 0.019 | 0.017 | 0.027 |
| After 24 hours | Probe tack [N] | 0.61 | 0.65 | 0.56 |
|  | Peel strength [N] | 0.035 | 0.035 | 0.104 |
|  | Loss modulus [Pa] | 5,435 | 5,666 | 5,614 |

Reference Examples 8 to 11

Gel patches (Reference Examples 8 to 11) were produced in the same manner as in Reference Example 1 except that diclofenac sodium, indometacin, felbinac or flurbiprofen was used in place of ketoprofen. All of the gel patches of Reference Examples 8 to 11 showed favorable results in Tests 1 to 4.

The invention claimed is:

1. A gel patch having a paste layer on a support,
wherein the paste layer comprises ketoprofen or a pharmaceutically acceptable salt thereof, propylene glycol, 1-menthol, and water, and further comprises a fatty acid alkyl ester,
wherein a mass of propylene glycol in the paste layer is 3-fold the mass of ketoprofen or less,
wherein the fatty acid alkyl ester comprises at least one selected from the group consisting of hexyl laurate and isopropyl palmitate, and
wherein the content of 1-menthol based on a total mass of the paste layer is 0.1 to 0.5 mass %.

2. A method of stabilizing ketoprofen in a gel patch having a paste layer comprising ketoprofen, propylene glycol, 1-menthol, and water, and further comprises a fatty acid alkyl ester on a support,
wherein the content of 1-menthol based on a total mass of the paste layer is 0.1 to 0.5 mass %, and
wherein the fatty acid alkyl ester comprises at least one selected from the group consisting of hexyl laurate and isopropyl palmitate,
the method comprising incorporating a mass of propylene glycol 3-fold the mass of ketoprofen or less into the paste layer.

* * * * *